(12) United States Patent
Xu et al.

(10) Patent No.: US 10,378,033 B2
(45) Date of Patent: Aug. 13, 2019

(54) CONVERTING BIOMASS TO FERMENTATIVE PRODUCTS

(71) Applicant: BASF Corporation, Florham Park, NJ (US)

(72) Inventors: Haowen Xu, Yorktown Heights, NY (US); Sharad Mathur, Tega Cay, SC (US); Karin Arens, Bonaire, GA (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 15/566,524

(22) PCT Filed: Apr. 12, 2016

(86) PCT No.: PCT/US2016/027130
§ 371 (c)(1),
(2) Date: Oct. 13, 2017

(87) PCT Pub. No.: WO2016/168195
PCT Pub. Date: Oct. 20, 2016

(65) Prior Publication Data
US 2018/0100174 A1  Apr. 12, 2018

Related U.S. Application Data

(60) Provisional application No. 62/146,571, filed on Apr. 13, 2015.

(51) Int. Cl.
| | |
|---|---|
| *C04B 40/00* | (2006.01) |
| *C04B 14/10* | (2006.01) |
| *C04B 18/24* | (2006.01) |
| *C04B 20/04* | (2006.01) |
| *C04B 103/00* | (2006.01) |
| *C12P 19/14* | (2006.01) |
| *C08B 37/00* | (2006.01) |
| *C12N 9/42* | (2006.01) |
| *C12P 19/02* | (2006.01) |
| *D21C 1/04* | (2006.01) |
| *D21C 5/00* | (2006.01) |

(52) U.S. Cl.
CPC ............ *C12P 19/14* (2013.01); *C04B 14/106* (2013.01); *C04B 18/24* (2013.01); *C04B 40/0039* (2013.01); *C08B 37/0003* (2013.01); *C12N 9/2434* (2013.01); *C12P 19/02* (2013.01); *D21C 1/04* (2013.01); *D21C 5/005* (2013.01); *C04B 2103/0088* (2013.01); *C12P 2201/00* (2013.01); *C12P 2203/00* (2013.01); *C12Y 302/01* (2013.01); *Y02E 50/16* (2013.01); *Y02W 30/97* (2015.05)

(58) Field of Classification Search
CPC ....... C12P 19/14; C12P 19/02; C12P 2201/00; C12P 2203/00; C04B 40/0039; C04B 14/106; C04B 18/24; C04B 2103/0088; D21C 5/005; D21C 1/04; C12N 9/2434; C08B 37/0003; C12Y 302/01
See application file for complete search history.

(56) References Cited

U.S. PATENT DOCUMENTS

| | | | | |
|---|---|---|---|---|
| 7,749,476 | B2 * | 7/2010 | Constantz | ............. C01B 33/187 |
| | | | | 205/477 |
| 8,871,739 | B2 * | 10/2014 | Blair | ....................... C07H 3/02 |
| | | | | 514/53 |
| 2010/0113764 | A1 | 5/2010 | Blair et al. | |
| 2015/0202607 | A1 * | 7/2015 | Geremia | ............. C13K 13/002 |
| | | | | 127/37 |

FOREIGN PATENT DOCUMENTS

| | | |
|---|---|---|
| DE | 10 2009 016001 A1 | 10/2010 |
| WO | 2009/061750 A1 | 5/2009 |

OTHER PUBLICATIONS

Lenarda et al., Solid acid catalysts from clays: preparation of mesoporous catalysts by chemical activation of metakaolin under acid conditions. J. Colloid. Interface Sci., 2007, vol. 311: 537-543. (Year: 2007).*

Prasetyo et al., Efficient cellulase-catalyzed saccharification of untreated paper sludge targeting for biorefinery. Biomass and Bioenergy, 2010, vol. 34: 1906-1913. (Year: 2010).*

Tan, Inn Shi et al. "Solid acid catalysts pretreatment and enzymatic hydrolysis of macroalgae cellulosic residue for the production of bioethanol", Carbohydrate Polymers, vol. 124, Mar. 3, 2015, pp. 311-321.

Guo, Feng et al. "Solid acid mediated hydrolysis of biomass for producing biofuels", Progress in Energy and Combustion Science, Elsevier Science Publishers, Amsterdam, NL, vol. 38, No. 5, Dec. 26, 2011, pp. 672-690.

International Search Report and Written Opinion dated Aug. 18, 2016, from International Application No. PCT/US2016/027130, 15 pages.

\* cited by examiner

*Primary Examiner* — Ganapathirama Raghu
(74) *Attorney, Agent, or Firm* — Meunier Carlin & Curfman LLC

(57) ABSTRACT

The present application relates to reaction mixtures comprising biomass, a solid acid catalyst and cellulolytic enzymes or organisms expressing such enzymes for converting biomass to useful feedstocks and methods of forming products via fermentation using the said reaction mixture.

15 Claims, 2 Drawing Sheets

CONVERTING BIOMASS TO FERMENTATIVE PRODUCTS

CROSS-REFERENCE TO RELATED APPLICATIONS

This application is a national stage application filed under 35 U.S.C. § 371 of PCT/US2016/027130 filed Apr. 12, 2016, which claims the benefit of U.S. Provisional Application No. 62/146,571 filed Apr. 13, 2015 which is hereby incorporated in its entirety and for all purposes.

FIELD OF THE DISCLOSURE

The present application relates to reaction mixtures comprising biomass, a solid acid catalyst and celluloytic enzymes for converting biomass to useful feedstocks and methods of forming products via fermentation using the said reaction mixtures.

BACKGROUND OF THE DISCLOSURE

The terms "biomass" refers to any non-fossilized, i.e., renewable, organic matter. The various types of biomass include plant biomass (defined below), animal biomass (any animal by-product, animal waste, etc.) and municipal waste biomass (residential and light commercial refuse with recyclables such as metal and glass removed).

The conversion of these inexpensive biomass materials have been studied extensively for use as a feedstock for fermentation products. In order for the microorganisms to use these biomass feedstocks, the feedstocks need to be broken down into sugars which may be easily used by the microorganisms.

Pretreatment of cellulosic biomass has been regarded as a necessary step to allow accessibility of cellulolytic enzyme to its substrates, cellulose and hemicellulose within the rigid cell wall structure. Many pretreatment technologies have been developed over years to reduce the recalcitrance of cellulosic biomass structure and most of them involve some form of chemical treatment in a liquid phase under high temperature and high pressure conditions. Sulfuric acid is one of the most commonly added chemicals because it is less expensive compared to other chemicals such as base or solvent and it can result in an effective solubilization of hemicellulose.

Concentrated sulfuric acid can be utilized to solubilize both cellulose and hemicellulose to monomer sugars, however the process normally suffers from low hydrolysis yield due to formation of large amount of degradation products and subsequently very low fermentation yield because most of these degradation products are very inhibitory to fermentation organisms. Therefore, most of acid pretreatment is conducted at low concentrations of sulfuric acid. However, significant drawbacks exist. First, the hemicellulose fraction can be readily hydrolyzed to monomeric sugars by dilute acid. However, the cellulose and lignin fractions remains almost unaltered and significant amount of enzyme is normally needed to break down the insoluble cellulose fraction in an additional enzymatic hydrolysis step. Secondly, dilute acid pretreatment is normally performed in a liquid phase reactor under high temperature and high pressure conditions. Sufficient amount of water is required or a presoaking step is necessary to ensure the best mixing of acid catalyst and biomass. Because of the strong corrosion effects of dilute acid under these conditions, very expensive construction material for reactors is normally required. Finally, the acid must be neutralized before an enzymatic hydrolysis or fermentation step can take place. Formation of large amount of gypsum could be problematic to downstream processing when neutralized with inexpensive calcium hydroxide. Accordingly, there is a need for a more efficient and inexpensive methods of making lignocellulosic materials suitable for producing fermentable sugars for the biosynthetic production of various fermentation products.

SUMMARY OF THE DISCLOSURE

The inventors have discovered that solid acid catalysts can hydrolyze both cellulose and hemicellulose fractions of biomass into oligomeric sugars in a solid phase reaction. More importantly, the inventors have also discovered that when cellulolytic enzymes are used to breakdown oligomeric sugars and residual insoluble biomass materials or/and fermentative organisms are applied to convert sugars into various fermentation products, the presence of a solid acid catalyst does not inactivate the enzyme(s) and/or the organisms. Therefore the removal of the solid acid catalyst is avoided during enzymatic hydrolysis and/or fermentation, a significant savings in capital investment and processing costs for biomass conversion processes.

Thus the inventors disclose both a reaction mixture useful for effective hydrolysis of biomass materials and methods for: breaking down biomass and converting into usable sugars and biosynthetically preparing a feedstock for use in the fermentation of a product. Thus this application is directed to several methods.

A method of releasing saccharides from a biomass comprising the steps: a) pre-treating a biomass with a solid acid catalyst, b) forming an aqueous reaction mixture comprising the pre-treated biomass, solid acid catalyst, and one or more cellulase and/or hemicellulase enzymes or mixtures thereof; or an organism capable of expressing one or more cellulase and/or hemicellulase enzymes.

A method of biosynthetically preparing a product comprising the steps: a) pre-treating a biomass with a solid acid catalyst, b) forming an aqueous reaction mixture comprising the pre-treated biomass, solid acid catalyst and one or more cellulase and/or hemicellulase enzymes or mixtures thereof or an organism capable of expressing one or more cellulose and/or hemicellulase enzyme and c) culturing a prokaryote or eukaryote organism in the presence of the reaction mixture in step b) or an aqueous extract of the reaction mixture in step b) to form the product.

A biosynthetic reaction mixture comprising a) a pre-treated biomass with solid acid catalyst and b) one or more cellulase and/or hemicellulase enzymes or combinations thereof or an organism capable of expressing one or more cellulose and/or hemicellulase enzyme.

A pozzolanic material is also disclosed prepared from a method comprising a) pre-treating a biomass with a kaolin solid acid catalyst. The method of preparing the pozzolanic material can further comprises the steps of b) forming an aqueous reaction mixture comprising the pre-treated biomass, kaolin solid acid catalyst of step a), and one or more cellulases and/or hemicellulase enzymes or mixtures thereof or an organism capable of expressing one or more cellulases and/or hemicellulase enzymes; and c) isolating the kaolin solid acid catalyst to provide the pozzolanic material. The method can also include heating the kaolin to form metakaolin.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DETAILED DESCRIPTION

Figure 1:
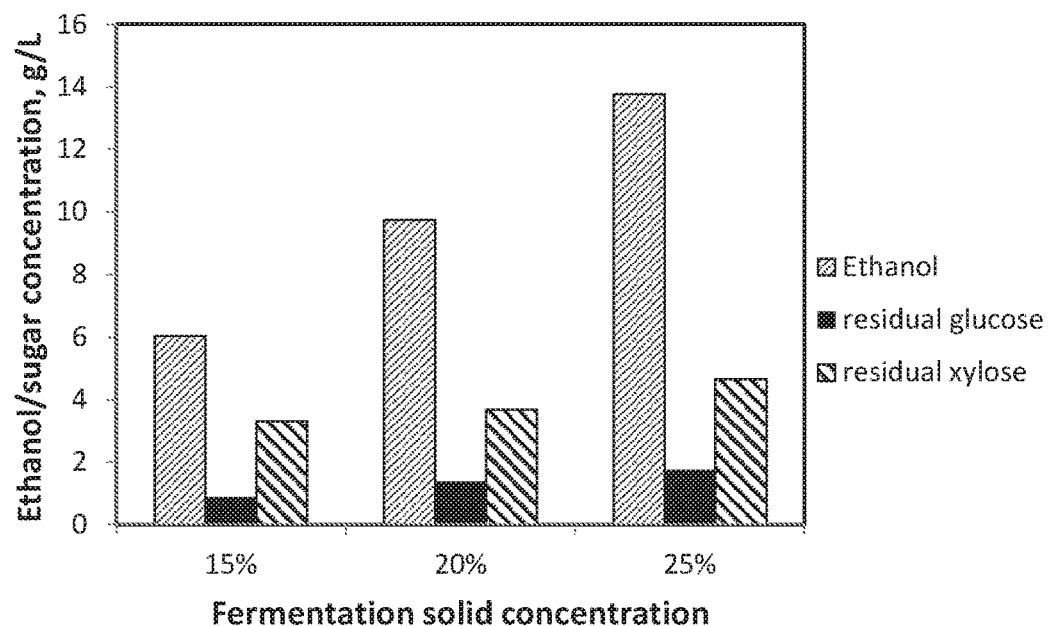
FIG. 1 is a graph showing simultaneous saccharification and fermentation process using the milled dry biomass and the kaolin clay mixture in Example 1.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise. The disclosure of percentage ranges and other ranges herein includes the disclosure of the endpoints of the range and any integers provided in the range.

Biomass

Biomass refers to virtually any plant-derived organic matter (woody or non-woody) available for energy on a sustainable basis. Plant biomass can include, but is not limited to, corn, agricultural crop wastes and residues such as corn stover, wheat straw, rice straw, sugar cane bagasse, and the like. Plant biomass further includes, but is not limited to, trees, woody energy crops, wood wastes and residues such as softwood forest thinnings, barky wastes, sawdust, paper and pulp industry waste streams, wood fiber, and the like. Additionally grass crops, such as switchgrass and the like have potential to be produced on a large-scale as another plant biomass source. For urban areas, the best potential plant biomass feedstock includes yard waste (e.g., grass clippings, leaves, tree clippings, and brush) and vegetable processing waste. "Lignocellulosic feedstock," is any type of plant biomass such as, but not limited to, non-woody plant biomass, cultivated crops, such as, but not limited to, grasses, for example, but not limited to, C4 grasses, such as switchgrass, cord grass, rye grass, miscanthus, reed canary grass, or a combination thereof, or sugar processing residues such as bagasse, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the cellulosic feedstock may include cellulosic waste material such as, but not limited to, newsprint, cardboard, sawdust, and the like.

If the biomass material is a lignocellulosic material it will have a cellulose, hemicellulose, and lignin content. Typically, in such lignocellulosic material, the cellulose, hemicellulose, and lignin are bound together in a complex gel structure along with small quantities of extractives, pectins, protein, and ash. Generally, lignocellulosic material is poorly accessible to microorganisms, enzymes and the like that are used to hydrolyze cellulose.

Solid Acid Catalyst

The solid acid material may be any solid material having a surface acidity. By "solid," it is meant a solid material, a semi-solid material, or any other material having a water content of less than about 15, 20, 25, 30 or 40 percent by weight. Surface acidity refers to the acidity of the solid surface of the material. Surface acidity determination methods are founded on the adsorption of a base from the base's solution. The amount of base that will cover the solid surface of the solid acid material with a monolayer is defined as the surface acidity and corresponds to the $pK_a$ of the base used. The base used may be n-butylamine, cyclohexamine, or any other suitable base. The degree of surface acidity is typically expressed by the Hammet and Deyrups $H_0$ function:

$$H_0 = pK_{BH^+} - \log(C_{BH^+}/C_B) \quad (I).$$

Thus, in this equation, when an indicator, B, is adsorbed on an acid site of the solid surface of the material, a part of the indicator is protonated on the acid site. The strength of the acid sites may be represented by Formula (I) by the value of $pK_{BH^+}$ of $BH^+$. $BH^+$ is the conjugate acid of indicator B when the concentration of $BH^+$ ($C_{BH^+}$) is equal to the concentration of B ($C_B$). Therefore, the acid strength indicated by $H_0$ shows the ability of the conjugate to change into the conjugate acid by the acid sites that protonates half of the base indicator B. Under a Lewis definition, the $H_0$ value shows the ability that the electron pair can be received from half of the absorbed base indicator B. See Masuda et al., Powder Technology Handbook, 3rd Ed. (2006). A $H_0$ of −8.2 corresponds to an acidity of 90 percent sulfuric acid and a $H_0$ of −3.0 corresponds to an acidity of about 48 percent sulfuric acid.

Any suitable method of determining the $H_0$ of a material may be used, such as the method using the adsorption of n-butylamine from its solution in cyclohexane as set forth in *Investigation of the Surface Acidity of a Bentonite modified by Acid Activation and Thermal Treatment*, Turk. J. Chem., 2003; 27:675-681, the disclosure of which is hereby incorporated by reference in its entirety. Alternatively, indicators, generally referred to as Hammett indicators, may be used to determine the $H_0$ of a material. Hammett indicators rely on color changes that represent a particular surface acidity of the subject material.

In the present invention, a number of solid acid materials may be used. Generally, the solid acid material in the present invention may be any solid material having a surface acidity. Preferably, the solid acid material has an $H_0$ of less than about −3.0, and preferably less than about −5.6.

In one embodiment, the solid acid material is a clay material. As used herein, "a clay material" is defined as a material composed primarily of fine-grained minerals, which is generally plastic at appropriate water contents and will harden when dried or fired. Exemplary minerals that comprise the major proportion of clay materials for use in the present invention include kaolinite or kaolin, halloysite, attapulgite, montmoirllonite, illite, nacrite, dickite, and anauxite. Non-limiting examples of clays for use in the present invention include fuller's earth, kaolin, and bentonite. Kaolin is a clay material that mainly consists of the mineral kaolinite. Bentonite is a clay containing appreciable amounts of montmorillonite, and typically having some magnesium and associated therewith. Optionally, the clay material may be acid-treated to provide further surface acidity to the clay material.

In another embodiment, the solid acid material is any aluminosilicate (a subset of clays) or hydrated aluminosilicate mineral. For example, the solid acid may be vermiculite, muscovite mica, kaolinite, metakaolin, halloysite, attapulgite, montmorillonite, illite, nacrite, dickite, and anauxite, or zeolites such as analcime, chabazite, heulandite, natrolite, phillipsite, and stilbite, or any mineral having the general formula $Al_2O_3.xSiO_2.nH_2O$.

In another embodiment, the solid acid material is a superacid material. Superacid materials are useful in the present invention because of the high number of acidic sites on the surface of the superacid material. Broensted superacids may be described as acids which are stronger than 100 percent sulfuric acid. Lewis superacids may be described as acids that are stronger than anhydrous aluminum trichloride. Solid superacids are composed of solid media, i.e. alumina, treated with either Bröensted or Lewis acids. The solids used may include natural clays and minerals, metal oxides and sulfides, metal salts, and mixed metal oxides. Exemplary Bröensted superacids include titanium dioxide:sulfuric acid ($TiO_2:H_2SO_4$) and zirconium dioxide:sulfuric acid ($ZrO_2:H_2SO_4$) mixtures. Exemplary Lewis superacids involve the incorporation of antimony pentafluoride into metal oxides, such as silicon dioxide ($SbF_5:SiO_2$), aluminum oxide ($SbF_5:Al_2O_3$), or titanium dioxide ($SbF_5:TiO_2$). In one embodiment, the superacid is a metal oxide treated with either Bröensted or Lewis acids. In a particular embodiment, the superacid is alumina treated with sulfuric acid or methanesulfonic acid as set forth below.

Alternatively, the solid acid material may be a silicate material, such as talc or any other suitable solid material having a surface acidity, such as alumina, and combinations of any of the materials described herein.

In one embodiment, the solid acid material is kaolin. Kaolin is composed primarily of the mineral kaolinite. Kaolinite ($Al_2Si_2O_5(OH)_4$) is a layered silicate made of alternating sheets of octahedrally coordinated aluminum and tetrahedrally coordinated silicon that are bonded by hydroxyl groups. Alternatively, the solid acid may be in the form of anhydrous kaolin, which may be prepared by heating kaolin typically above 500 degrees centigrade. In another embodiment the kaolin may be heat treated or steam treated to increase the surface acidity. For example, the kaolin may be converted to metakaolin and used as the solid acid catalyst.

Additionally, the solid acid catalyst, for example kaolin or metakaolin may be crushed to form smaller particles and increase surface area thus increasing its acidity.

In another embodiment, the solid acid is bentonite, for example an acidified bentonite. Bentonite is an absorbent aluminum phyllosilicate generally impure clay consisting mostly of montmorillonite, $(Na,Ca)_{0.33}(Al,Mg)_2Si_4O_{10}(OH)_2.(H2O)_n$. Two types exist: swelling bentonite which is also called sodium bentonite and non-swelling bentonite or calcium bentonite.

The acidified bentonite may be prepared by treating bentonite with one or more acids, such as by treating bentonite with 1 M hydrochloric acid solution.

In still another particular embodiment, the solid acid is a solid superacid comprising alumina treated with 2 M sulfuric acid, filtered and calcined at about 800 degrees centigrade for about 5 hours.

Kaolin and acidified bentonite are desirable materials for use in the present invention because they provide a high surface acidity along with an inherent amount of water, both due to presence of structural and surface hydroxyl groups and a free water content, which are both useful to hydrolyze the glycosidic bonds of the cellulose material. Therefore, using acidified bentonite, bentonite, metakaolin and kaolin as the solid acid material can provide a substantial benefit as the use of the materials may eliminate the need for added water to the solubilization process, thereby significantly decreasing time and expense in the solubilization of cellulose.

In another embodiment, the solid acid material is an acid-treated material, such as sulfuric acid-treated alumina to form a superacid. To prepare this superacid, alumina was stirred in 2 M sulfuric acid, filtered and calcined at about 800 degrees centigrade for about 5 hours. Treating the alumina with sulfuric acid adds sulfate ions to the solid alumina surface, thereby allowing the solid acid material to further accept electrons. As a result, these superacids have a very high surface acidity. However, while superacids may have a higher surface acidity than bentonite or kaolinite, the superacids may not have as much water present. As a result, while not wishing to be bound by theory, it appears the additional water content found in kaolin and bentonite contributes to the higher solubilization efficiency for cellulose found with bentonite or kaolonite over acid-treated alumina. This statement is further supported in showing that the solubilization efficiency is lower for anhydrous kaolinite vs. kaolin, which has a higher water content.

Thus the presently disclosed methods which requires a) pre-treating a biomass with a solid acid catalyst, the solid acid catalyst is any solid material having a surface acidity. In one embodiment the solid acid catalyst is a clay, an aluminosilicate, hydrated aluminosilicate or solid media treated with Brönsted or Lewis acids. In another embodiment the solid acid catalyst is selected from the group consisting of kaolinite, halloysite, attapulgite, monmoirllonite, illite, nacrite, dickite, annauxite, kaolin, metakaolin, bentonite, acidified betonite zeolites, titanium dioxide treated with sulfuric acid or methanesulfonic acid, aluminum oxide treated with sulfuric acid or methanesulfonic acid, alumina, alumina treated with sulfuric acid or methanesulfonic acid, vermiculite, muscovite mica and talc.

As explained above the biomass is pre-treated with the solid acid catalyst. This pre-treatment will often involve grinding, milling or shearing of the biomass with solid acid catalyst and is carried out often under relatively dry conditions.

Step a)

While the pre-treatment step requires some water in order to hydrolyze the cellulose or hemicellulose, the pre-treatment step a) should be carried out with a minimum of water present.

What is meant by "minimum of water" or "essentially dry" is the total water content from the biomass and the solid acid catalyst during the pre-treatment stage (step a) will range from about 0.1 to about 40 weight % water present, for example about 0.2 to about 25 weight % or about 0.5 to about 20 weight % and the weight % is based on the total weight of the biomass and solid acid catalyst.

In another embodiment the free water content of the solid acid material is in the range of about 4 percent to about 10 percent by weight of the solid acid material in step a). This free water content of the solid acid material is based on the total weight of the solid acid material and the moisture content. For example if the solid acid material containing moisture weights 100 g and contains 10% moisture, then the free water content of the 100 g is 10 g.

One of the advantages of using the solid acid material over say for example, sulfuric acid is that in relatively dry state grinding of the solid acid with the biomass, the cellulose and the hemicellulose are efficiently broken down. But once water is added to the pre-treated biomass, the acidity of the system is significantly reduced such that little adjustment of pH is required for enzyme and microbes action. Accordingly, the solid acid is rendered benign to the enzyme and microbes. Additionally, as no pH adjustment is required, no salt by-products are generated. The total free water content of the cellulose-containing material and the solid acid material is collectively less than about 40 percent by weight, and typically from about 2 percent to about 30 percent by weight, so as to not undesirably lower the kinetic energy needed for the hydrolysis reaction upon agitating during the pre-treatment step a). By "free water content," it is meant an amount of water in the cellulose-containing material and solid acid containing material that is contained within the cellulose-containing material and the solid acid material, but does not pertain to structural or surface hydroxyls of either material. In this way, there is sufficient water in the mixture to drive the hydrolysis reaction.

The grinding, milling or shearing may be carried out by any method known in the art. For example, the agitation may take place in any suitable vessel or reactor. In one embodiment, the agitating takes place in a ball, roller, jar, hammer, or shaker mill. The mills generally grind samples by placing them in a housing along with one or more grinding elements and imparting motion to the housing. The housing is typically usually cylindrical and the grinding elements are typically steel balls, but may be rods, cylinders, or other shapes.

In some cases the solid acid catalyst is heated during the pre-treatment step in the presence of the biomass (step a) to temperatures ranging from above room temp 20° C. to about 160° C., for example about 40° C. to about 120° C. in step a).

Ratio of Biomass to Solid Acid Catalyst

The weight ratio of the biomass to solid acid catalyst used may vary widely depending on biomass type, grinding technology and process parameters. For example, the wt. ratio of the dry solid acid catalyst and dry biomass ranges from about 0.1 to about 10 to about 10 to about 0.1, for example about 0.2 to about 5 to about 5 to about 0.2, and for example about 0.5 to about 2 to about 2 to about 0.5. A particular weight ratio of interest is about 1 to about 2 to about 2 to about 1.

Further what is meant by "dry" solid acid catalyst or "dry" biomass means that the catalyst and the biomass will likely contain some water but the water content from the biomass and the solid acid catalyst will range as above. That is the total water content from the biomass and the solid acid catalyst during the pre-treatment stage (step a) will range from 0.1 to about 40 weight % water present, for example about 0.2 to about 25 weight % or about 0.5 to about 20 weight % and the weight % is based on the total weight of the biomass and so and the weight % is based on the total weight of the biomass and solid acid catalyst. In order to hydrolyze the cellulosic material some water must be present. This water could be directly added to the pre-treatment step or could simply be present in the solid materials (biomass and solid acid catalyst).

After pre-treatment step a), water may added to the pre-treated biomass with solid acid catalyst. The water may be hot water ranging from about 80° C. to about 240° C. The hot water treatment may be advantageous between steps a) and b) as this may extract additional lignin and sugars from the biomass matrix before adding cellulase or hemicellulase enzymes or organisms expressing these enzymes.

Step b)

Once the biomass is pre-treated with the solid acid catalyst (step a), water is added to the pre-treated biomass with solid acid catalyst to form an aqueous reaction mixture comprising the pre-treated biomass, solid acid catalyst in step b). This is needed in order for the enzyme to carry out its hydrolyzing function. Further the addition of water raises the pH of the reaction mixture. Step (b) is normally run at temperatures conducive to the enzymes. In the second step (b) the temperature ranges from about 20° C. or 30° C. to about 75° C. once the enzymes are added.

The solid acid catalyst and biomass may be subjected to treatment with proteins such as Bovine Serum Albumin (BSA) and or surfactants such as Tween 80 and Tween 20 prior to or together with treatment with the enzyme in step b).

These additives may allow for lower concentrations of enzymes or more effective use of the enzymes during hydrolysis of the biomass.

Step b) is as suggested run under aqueous conditions. The concentration of solids (Biomass, solid acid catalyst) in step (b) will range from about 10 to about 60 wt. % solids. For example, about 12 to about 45 wt. % solids, about 15 to about 40 wt. % solids are envisioned. The wt. % solids is based on the total weight of the reaction mixture.

The advantage of step (b), is the solid acid catalyst does not need to be removed from the pre-treated biomass in step (a) before the enzymes of interest or the organism expressing a cellulase and/or hemicellulase enzyme or enzymes is added. In fact, there appears to be decided advantages in retaining the presence of the solid acid catalyst in the presence of the enzymes or organism expressing a cellulase and/or hemicellulase enzyme.

After step b) is completed, the reaction mixture may be filtered to remove the solid acid catalyst, enzymes, organisms expressing the cellulase and/or hemicellulase enzymes or residual biomass. Alternatively, the residual solids of step b) along with the spent reaction mixture may be combined with a fermentation or culturing medium directly to produce a product. Carrying the solid acid catalyst through to step c) will not interfere with the fermentation biosynthesis process.

Thus the removal of the solid acid catalyst is optional before step c).

Enzymes

Cellulose and hemicellulose are the first and second most abundant polysaccharides in nature. Cellulose represents anywhere from 30 to 60% while hemicelluloses represent about 20-35% of lignocellulosic biomass (LBM) such as hardwoods, softwoods, corn fiber, corn stover, wheat straw, rice straw, and sugarcane bagasse. While cellulose is an almost homogeneous polymer comprised of several hundreds to thousands D-glucose units linked through 1,4 .beta.-glycosidic linkages, hemicelluloses are heterogeneous polymers of pentoses (xylose, arabinose), hexoses (mannose, glucose, galactose), and sugar acids. Hardwood hemicelluloses contain mostly xylans, whereas softwood hemicelluloses contain mostly glucomannans. Xylans of most plant materials are thus heteropolysaccharides with homopolymeric backbone chains of 1,4-linked .beta.-D-xylopyranose units. Besides xylose, xylans may also contain arabinose; glucuronic acid or its 4-O-methyl ether; and acetic, ferulic, and p-coumaric acids. The frequency and composition of branches are dependent on the source of xylan while the backbone consists of O-acetyl, .alpha.-arabinofuranosyl, .alpha.-1,2-linked glucuronic or 4-O-methylglucuronic acid substituents.

For both cellulose and hemicellulose components to be efficiently converted to their mono, di or oligomeric sugar components these must first be extracted from the lignocellulosic/cellulosic complex. The pre-treatment step (a) helps to extract the complex. The enzymatic saccharification of these components using cellulases and hemicellulases in the presence of the solid acid catalyst (step b) further breaks down the saccharides with negligible substrate loss and side product generation.

While cellulose, though a homopolymer, is a far more bulkier, crystalline and compact molecule, the structure of hemicellulose is more complex as it comprises of pentoses, some hexoses and side chain groups such as acetyl and uronic acids. Thus, enzymatic hydrolytic action for both cellulose and hemicellulose requires combined action of more than one enzyme. For cellulose hydrolysis the crystal structure of cellulose needs to be partially or wholly rendered amorphous after which a mixture of exo, endo cellulases and cellobiases is required for conversion of the polymeric cellulose to much smaller oligomeric and monomeric molecules. On the other hand, in case of hemicellulose, the presence of side chain groups hampers the action of major backbone depolymerizing enzymes i.e. exo and endo xylanases, and mannanases. To address this problem, accessory enzymes such as .alpha.-L-arabinofuranosidase, .alpha.-glucuronidase, acetylxylan esterase, ferulic acid esterase, and p-coumaric acid esterase which have the ability to hydrolyze the side chains may to be present with the major hemicellulases to achieve complete degradation of hemicellulose to obtain high yields of monosaccharide sugars (Biely and Tenkanen, 1998).

Thus the cellulase and hemicellulase preparations used for depolymerizing or hydrolyzing cellulose and hemicellulose, respectively, contain a myriad of major and minor enzymes that all act together.

The loading of cellulase and/or hemicellulase in step b) will vary considerable. Cellulolytic enzymes using recombinant technology can also be used. Treatment of the pretreated cellulose/hemicellulose with cellulase/hemicellulase is usually carried out at temperatures between 20° C. and 75° C. Cellulases are active over a range of pH of about 3 to 7. A saccharification step may last up to 144 hours. The cellulose/hemicellulose enzyme dosage achieves a sufficiently high level of cellulose and hemicellulose conversion. For example, an appropriate cellulose/hemicellulase dosage is typically between 1 and 50 Filter Paper Units (FPU or IU) per gram of cellulose. The FPU is a standard measurement and is defined and measured according to Ghose (1987, Pure and Appl. Chem. 59:257-268). Further, it is possible in step b) to combine the treated biomass of step a) with an organism which expresses one or more cellulase and/or hemicellulase enzymes. This may be carried out in the presence of the solid acid catalyst. There is no need to remove the solid acid catalyst after treatment of the biomass in step a) as it does not have a negative effect on the organism expressing the cellulose and/or hemicellulase enzyme or enzymes.

This organism expressing the cellulose and/or hemicellulose enzyme may be the same prokaryote or eukaryote producing the product in step c). See below.

Prokaryote or Eukaryote

When a microorganism is utilized to biosynthetically produce a product, it can be a natural microorganism or an engineered microorganism (e.g., a genetically modified microorganism (GMO)). For example, the microorganism can be a bacterium, e.g., a cellulolytic bacterium, a fungus, e.g., a yeast, a plant or a protist, e.g., an algae, a protozoa or a fungus-like protist, e.g., a slime mold, protists (e.g., animal (e.g., protozoa such as flagellates, amoeboids, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, mesoplankton, microplankton, nanoplankton, picoplankton, and femptoplankton), phytoplankton, and/or mixtures of these. In some embodiments, the microorganism is white rot fungus. In some instances, the microorganism can include unicellular and/or multicellular organisms. When the organisms are compatible, mixtures can be utilized.

Generally, various microorganisms can produce a number of useful products by operating on, converting, bioconverting, or fermenting the materials. For example, alcohols, organic acids, hydrocarbons, hydrogen, proteins, carbohydrates, fats/oils/lipids, amino acids, vitamins, or mixtures of any of these materials can be produced by fermentation or other processes.

Examples of products that can be produced include mono- and polyfunctional C1-C6 alkyl alcohols, mono- and polyfunctional carboxylic acids, C1-C6 hydrocarbons, and combinations thereof. Specific examples of suitable alcohols include methanol, ethanol, propanol, isopropanol, butanol, ethylene glycol, propylene glycol, 1,4-butane diol, glycerin, and combinations thereof. Specific example of suitable carboxylic acids include formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid, .gamma.-hydroxybutyric acid, and combinations thereof. Examples of suitable hydrocarbons include methane, ethane, propane, pentane, n-hexane, and combinations thereof.

In some embodiments, the microorganism is a prokaryotic cell. Suitable prokaryotic cells include Gram-positive, Gram negative and Gram-variable bacterial cells, preferably Gram-negative.

Thus, microorganisms that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter parafineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantimum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas jhuorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis,*

*Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. sphaericum, Nostoc punctiforme, Spirulina platensis, Lyngbya majuscula, L. lagerheimii, Phormidium tenue, Anabaena* sp., *Leptolyngbya* sp and so forth.

In some embodiments, the microorganism is a eukaryotic cell. Suitable eukaryotic cells include yeast cells, as for example *Saccharomyces* sp., such as *Saccharomyces cerevisiae, Hansenula* sp., such as *Hansenula polymorpha, Schizosaccharomyces* sp., such as *Schizosaccharomyces pombe, Kluyveromyces* sp., such as *Kluyveromyces lactis* and *Kluyveromyces marxianus, Yarrowia* sp., such as *Yarrowia lipolytica, Pichia* sp., such as *Pichia methanolica, Pichia stipites* and *Pichia pastoris, Zygosaccharomyces* sp., such as *Zygosaccharomyces rouxii* and *Zygosaccharomyces bailii, Candida* sp., such as *Candida boidinii, Candida utilis, Cadida freyschussii, Candida glabrata* and *Candida sonorensis, Schwanniomyces* sp., such as *Schwanniomyces occidentalis, Arxula* sp., such as *Arxula adeninivorans, Ogataea* sp. such as *Ogataea minuta, Klebsiella* sp., such as *Klebsiella pneumonia.*

Numerous bacterial industrial strains are especially suitable for use in the methods disclosed herein. In some embodiments, the microorganism is a species of the genus *Corynebacterium*, e.g. *C. acetophilum, C. glutamicum, C. callunae, C. acetoacidophilum, C. acetoglutamicum.* In some embodiments, the microorganism is a species of the genus *Bacillus*, e.g., *B. thuringiensis, B. anthracis. B. megaterium, B. subtilis, B. lentils, B. circulans, B. pumilus. B. lautus, B.coagulans, B. brevis, B. firmus, B. alkaophius, B. licheniformis, B. clausii, B. stearothermophilus, B. halodurans, B. subtilis, B. pumilus*, and *B. amyloliquefaciens.* In some embodiments, the microorganism is a species of the genus *Erwinia*, e.g., *E. uredovora, E. carotovora, E. ananas, E. herbicola, E. punctata* and *E. terreus.* In some embodiments, the microorganism is a species of the genus *Escherichia*, e.g., *E. coli.* In other embodiments the microorganism is a species of the genus *Pantoea*, e.g., *P. citrea* or *P. agglomerans.* In still other embodiments, the microorganism is a species of the genus *Streptomyces*, e.g., *S. ambofaciens, S. achromogenes, S. avermitilis, S. coelicolor, S. aureofaciens, S. aureus, S. fungicidicus, S. griseus* or *S. lividans.* In further embodiments, the microorganism is a species of the genus *Zymomonas*, e.g., *Z. mobilis* or *Z. lipolytica.* In further embodiments, the microorganism is a species of the genus *Rhodococcus*, e.g. *R opacus.*

Fermentation

The fermentation conditions will vary depending about the organism, engineered or native. In some embodiments, the microorganisms used in step c) are grown under batch, fedbatch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is also possible and is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 34° C., 35° C. or 36° C. In a most preferred embodiment the temperature is about 37° C. or 38° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 60 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5 or 7.

Product of Fermentation

The product of the fermentation will depend upon the organism used to produce the product. There are many different organisms, both prokaryote and eukaryote known from the art to product various products such as methanol, ethanol, propanol, isopropanol, butanol, ethylene glycol, propylene glycol, 1,4-butanediol, glycerin, formic acid, acetic acid, propionic acid, butyric acid, valeric acid, caproic acid, almitic acid, stearic acid, oxalic acid, malonic acid, succinic acid or succinate, glutaric acid, oleic acid, linoleic acid, glycolic acid, lactic acid or lactate, gamma-hydroxybutyric acid, 3-hydroxyalkanoic acid, alanine, methane, ethane, propane, pentane, n-hexane, pyruvate, aspartate, malate, valine, leucine and combinations thereof.

Recycling of Solid Acid Catalyst

The solid acid catalyst can be recycled after step b). Alternatively, it can be carried through to the fermentation step c) in production of the product, separated from the product and reused.

If the catalyst is kaolin, an alternative use after separation in step b) or step c) is as a pozzolanic material in cementitious systems. Without wishing to be bound by theory, the mechanical work done on the kaolin surface can potentially disturb the surface crystallinity and allow use of this kaolin as pozzolanic material. The pozzolanic properties of the kaolin catalyst, after separation in step b) or step c) can be improved by burning at high temperatures to produce metakaolin. In some cases, lower thermal energy is needed to convert the used kaolin catalyst (i.e., after separation in step b) or step c)) to a pozzolanic metakaolin material compared to converting the un-used kaolin catalyst to metakaolin.

Metakaolin is a high value product produced from kaolin which serves as a pozzolanic material in cementitious systems. The pozzolanic activity of this metakaolin is significantly higher than the feed kaolin. This means that the metakaolin by product of the process used to convert cellulosic material into sugars through mechanochemical activation has a high sustainability advantage to cement-based systems.

Additionally, there could be other potential uses of kaolin mixed with lignin byproducts such as separation of lignin to derive value chemicals from the lignin or use of the mixture of kaolin and extracted lignin as a filler.

EXAMPLES

Example 1 Fermentation Process of Milled Biomass/Kaolin Powder

1. Screen sawdust with a number 8 mesh to remove large pieces of material.
2. Mix 25 g dry wt. of kaolin clay, a tertiary kaolin from Middle Georgia, 25 g dry wt. of mixed hardwoods sawdust, and 1600 g of grinding media, 3 mm yittria stabilized zirconium oxide.
3. Heat the water bath to 100° C.
4. Seal the mixing vessel and place it in the water bath.
5. Begin mixing using a mixing blade powered by a drill press.
6. Mix for 1 hour at 1920 rpm.
7. Stop dry milling.
8. Remove grinding media
9. Weigh out 3, 4 and 5 g of milled biomass and kaolin mixture into each fermentation bottle for fermentation conducted at 15%, 200/% and 25% solid concentrations, respectively.
10. Add 0.2 g yeast extract and 0.4 g tryptone into each fermentation bottle as fermentation nutrients.
11. Add 0.1 g calcium carbonate into each fermentation bottle as buffering agent.
12. Add water to each fermentation bottle to bring fermentation volume to 17.33 ml in each fermentation bottle; shake the bottles by hand and thoroughly mix the contents in the bottles.
13. Add 0.67 ml enzyme (Biocellulase W from Kerry) into each fermentation bottle.
14. Add 2 ml of *S. cerevisiae* seed culture (grown in a shake-flask for overnight) into each fermentation bottle.
15. Seal fermentation bottles with rubber stopper and aluminum seal.
16. Put fermentation bottles into 35° C. shaker, and shake at 200 rpm for 6 days.
17. At the end of fermentation, take samples from each bottle and submit for HPLC analysis to measure ethanol, glucose, xylose and byproduct concentrations.

FIG. 1 is a graph showing simultaneous saccharification and fermentation (SSF) process using milled dry biomass and dry kaolin clay mixture. Fermentation was conducted at 35° C. with yeast strain *S. cerevisiae* at 15%, 20% and 25% solid concentrations, respectively. Cellulase enzyme was loaded at 10 mg protein per gram of milled dry biomass. Total fermentation time is 144 h.

Example 2

Figure 2:
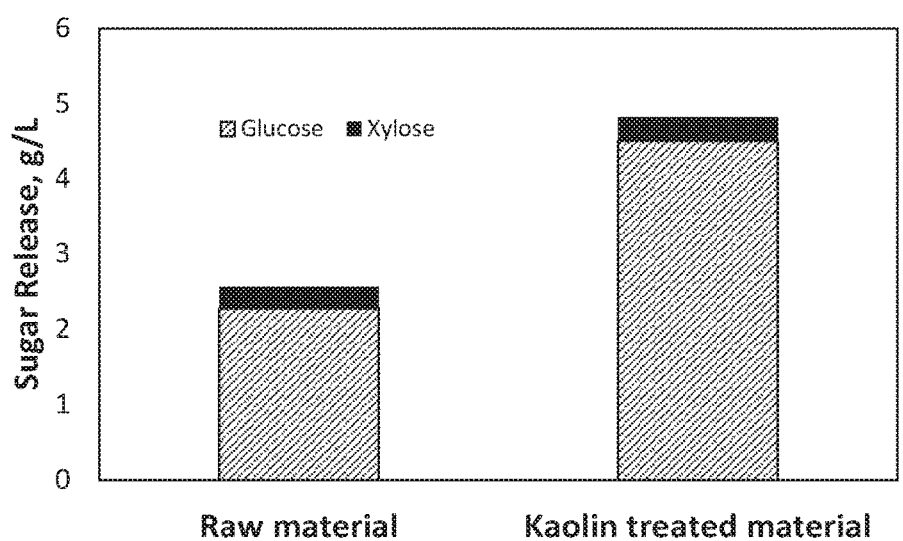
FIG. 2 is a bar graph showing enzymatic hydrolysis of the kaolin treated corn fibers in Example 2.

Corn fiber was ground with kaolin particles for 1 h at 100° C. in a corn fiber:kaolin weight ratio of 3:1. Enzymatic hydrolysis was carried out at 5% solids loading, an enzyme loading of 10 mg/g corn fiber, a temperature of 50° C., and the pH controlled at 5 with 50 mM of citrate buffer. Samples were taken at 24 h hydrolysis time and the concentration of glucose and xylose were determined by HPLC analysis. FIG. 2 is a bar graph showing enzymatic hydrolysis of the kaolin treated corn fibers.

Example 3

Figure 3:
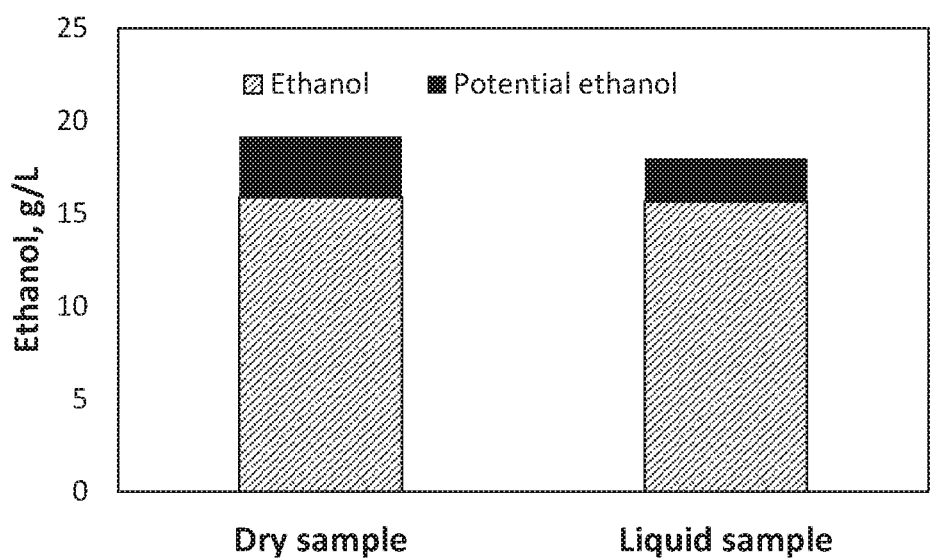
FIG. 3 is a bar graph showing a comparison of simultaneous saccharification and fermentation (SSF) with the dry ground saw dust sample and the liquid extract sample at equivalent biomass solid loading in Example 3.

A dry sample was produced by grinding saw dust sample and kaolin particles together for 1 h at 100° C. with a biomass/kaolin weight ratio of 1:1. A liquid extract was produced by adding boiling water to the ground dry kaolin/biomass mixture and stirring it for a set time at a constant temperature. SSF was conducted at 35° C. with yeast strain *S. cerevisiae* at 25% solid concentration, cellulase enzyme was loaded at 10 mg protein per gram of milled dry biomass. The total fermentation time was 144 h. Ethanol and residual sugars were measured by HPLC. Potential ethanol was calculated from residual sugars at 90% of theoretical conversion yield. FIG. 3 is a bar graph showing a comparison of SSF with the dry ground saw dust sample and the liquid extract sample at equivalent biomass solid loading.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative materials and method steps disclosed herein are specifically described, other combinations of the materials and method steps also are intended to fall within the scope of the appended claims, even if not specifically recited. Thus, a combination of steps, elements, components, or constituents may be explicitly mentioned herein, however, other combinations of steps, elements, components, and constituents are included, even though not explicitly stated.

What is claimed is:

1. A method of releasing saccharides from a biomass comprising the steps:
    a) pre-treating a biomass with a solid acid catalyst to form a solid acid catalyst mixture,
    b) forming an aqueous reaction mixture comprising the solid acid catalyst mixture of step a), and one or more cellulases and/or hemicellulase enzymes or mixtures thereof or an organism capable of expressing one or more cellulases and/or hemicellulase enzymes,
    wherein the solid acid catalyst is obtained from kaolin and the solid acid catalyst mixture is not purified prior to step b).

2. The method of claim 1, further comprising:
    c) culturing a prokaryote or eukaryote organism in the presence of the reaction mixture in step b) or an aqueous extract of the reaction mixture in step b) to form the product.

3. The method of claim 1, wherein the biomass is any plant-derived organic matter.

4. The method of claim 3, wherein the step a) is carried out with from about 0.1 to about 40 weight % water present.

5. The method of claim 1, wherein the wt. ratio of the dry solid acid catalyst to dry biomass ranges from about 0.1:10 to about 10:0.1.

6. The method of claim 1, wherein heat ranging from a temperature of from about 20° C. to about 160° C. is applied during the pre-treatment step a).

7. The method of claim 1, wherein water is added after the pre-treatment step a) but before addition of the enzyme in step b).

8. The method of claim 7, wherein the water added ranges in temperature from about 60° C. to about 240° C.

9. The method of claim 2, wherein the organism is a bacterium or a yeast.

10. The method of claim 1, wherein the solid acid catalyst and biomass are subjected to treatment with proteins and or surfactants prior to or together with treatment with the enzyme, step b).

11. The method of claim 2, wherein subsequent to step b) the solid acid catalyst is separated from reaction mixture of step b) to form an aqueous extract and the aqueous extract is cultured with the prokaryote or eukaryote organism to form the product.

12. The method of claim 2, wherein the culturing of the prokaryote or eukaryote organism to form the product occurs in the presence of the biomass, solid acid catalyst and enzymes of the reaction mixture of step b).

13. The method of claim 1, wherein the kaolin is isolated from the cultured product to provide a pozzolanic material.

14. The method of claim 13, wherein the kaolin isolated from the cultured product is burned to form metakaolin.

15. The method of claim 1, wherein step a) does not include the addition of water.

* * * * *